US007481973B2

(12) United States Patent
Beilfuss et al.

(10) Patent No.: US 7,481,973 B2
(45) Date of Patent: Jan. 27, 2009

(54) COMPOSITION AND PROCESS FOR CHEMICAL AND THERMAL DISINFECTION

(75) Inventors: Wolfgang Beilfuss, Hamburg (DE); Ralf Gradtke, Tornesch (DE); Peter Goroncy-Bermes, Hamburg (DE); Sabine Behrends, Pinneberg (DE); Michael Mohr, Kaltenkirchen (DE)

(73) Assignee: L'Air Liquide Sante International, Paris Cedex (FR)

( * ) Notice: Subject to any disclaimer, the term of this patent is extended or adjusted under 35 U.S.C. 154(b) by 540 days.

(21) Appl. No.: 10/825,266

(22) Filed: Apr. 15, 2004

(65) Prior Publication Data
US 2004/0208782 A1 Oct. 21, 2004

(30) Foreign Application Priority Data
Apr. 17, 2003 (DE) ............................ 103 17 931

(51) Int. Cl.
*A61L 2/18* (2006.01)
(52) U.S. Cl. .......................................... 422/28; 422/33

(58) Field of Classification Search ....................... None
See application file for complete search history.

(56) References Cited

U.S. PATENT DOCUMENTS

| 5,516,510 | A |   | 5/1996  | Beilfuss et al. |
|-----------|---|---|---------|-----------------|
| 5,539,001 | A | * | 7/1996  | Waldmann-Laue et al. .. 514/723 |
| 5,591,442 | A |   | 1/1997  | Diehl et al. |
| 5,686,045 | A | * | 11/1997 | Carter ......................... 422/20 |
| 5,906,802 | A | * | 5/1999  | Langford .................... 422/300 |
| 2003/0152644 | A1 | * | 8/2003 | Modak et al. ............... 424/667 |
| 2004/0001797 | A1 | * | 1/2004 | Saud et al. ............... 424/70.16 |

FOREIGN PATENT DOCUMENTS

| EP | 1 369 037 A1 | 5/2003 |
| GB | 2 103 089 A | 7/1982 |
| WO | WO92/09309 | * 6/1992 |

* cited by examiner

*Primary Examiner*—Elizabeth L McKane
(74) *Attorney, Agent, or Firm*—Young & Thompson

(57) ABSTRACT

A composition and process for the disinfection of the surface 0f an article which contains 1-(2-ethylhexyl)-glycerol ether for the disinfection of the surface of an article at a temperature above 25° C.

50 Claims, No Drawings

COMPOSITION AND PROCESS FOR CHEMICAL AND THERMAL DISINFECTION

BACKGROUND OF THE INVENTION

1. Field of the Invention

The present invention relates to the use of a composition which contains 1-(2-ethylhexyl)glycerol ether for thermochemical disinfection.

2. Related Art

Mechanical disinfection methods are employed for disinfecting instruments especially in the clinical sector. In these, an aqueous composition is allowed to act, normally at elevated temperature, on the surface to be disinfected, cf. Anforderungen an die Hygiene bei der Aufbereitung bei Medizinprodukten, Bundesgesund-heitsblatt 44 (2001), 1115-1126.

Preparations currently employed in thermochemical disinfection methods can be roughly divided into three groups:

Compositions which Contain Short-Chain Organic Acids Such as Formic Acid, Acetic Acid or Citric Acid.

The effect of such monobasic or polybasic acids is disclosed inter alia in EP-A-0 505 763 and AT-A-382 310, see also Hygiene+Medizin 1989, 14, pages 69 et seq., GB-A-2 103 089 and Tierärztliche Umschau 1988, 43, pages 646 et seq. It is additionally proposed in DE-C2-42 00 066 to employ a 1.5% by weight aqueous solution of citric acid, optionally with the addition of malic acid or lactic acid, to inactivate hepatitis B viruses. However, a disadvantage which has emerged is that such disinfectants necessarily have a low pH and accordingly, especially when relatively high temperatures are used for disinfecting instruments, act as strong corrosives.

Compositions Which Contain Quaternary Ammonium Compounds.

These have proved, especially in disinfectants with a very high alcohol content, e.g. in anhydrous isopropanol/n-propanol or 80% strength ethanol, to be effective hand disinfectants (see, inter alia, Wallhäuβer, Praxis der Sterilisation, Henkel Chemische Bibliothek, 4th edition, 1988, pages 75 et seq.). Disinfectants with a high alcohol content are, however, unsuitable for disinfecting instruments because they attack synthetic materials. In addition, disinfectants containing quaternary ammonium compounds are highly foaming, which restricts their use, especially for disinfecting instruments.

Compositions Which Contain Aldehydes Such as Formaldehyde, Acetaldehyde and Glutaraldehyde.

Aldehyde-containing disinfectants have been unwanted for some years because of the harmful effects on human health, especially of formalin, and because of their unpleasant odour.

Many materials (e.g. metal) of the surfaces of instruments (e.g. endoscopes) are moreover resistant to the agents used in known compositions for thermochemical disinfection for only a limited time and in a limited temperature range. Thus, known solutions used for thermochemical disinfection lead, at the temperatures necessary for use, to corrosion of the surfaces of treated articles, e.g. to rusting of metal, to hazing of glass, plastic or ceramics or to brittle synthetic materials. Replacement of the agents, lowering the concentration used and/or lowering the disinfection temperature are, however, subject to restrictions because the surface must be dependably cleaned and reliably disinfected and moreover a large number of microorganisms must be eliminated.

The disinfectant solutions conventionally employed, and corresponding concentrates, have disadvantages, however:

1. Many known agents are costly, leading to the respective disinfection method being uneconomic, especially if it is necessary to use high concentrations.
2. The known solutions for use must (i) contain comparatively high concentrations of agents, (ii) be employed at comparatively high temperatures and (iii) for a comparatively long time for dependable elimination of all relevant microorganisms. These three parameters are not unrestrictedly consistent with material-conserving disinfection and may lead to stress for the staff and/or environment from the solutions used.
3. Disinfectant concentrates are often not stable at low temperatures or on storage and are prone to discoloration and to foaming of the solutions prepared for use by dilution with water. To preclude these disadvantages of the concentrates it is necessary to add to the concentrates auxiliaries which are likewise subject to the restrictions described for the agents.
4. Many agents require the addition of appropriate auxiliaries for it to be possible to handle the agents in solutions diluted for use (and for example to afford solutions for use which are clear in the use concentration).
5. Many agents are effective only for certain micro-organisms. The formulation of disinfectants (solutions for use, concentrates) with three or more components in order to ensure efficacy for all relevant microbes leads to additional problems, however.
6. Many agents are unacceptable as residues even in small quantities, which is why careful rinsing of the disinfected surface with water is necessary. This procedure is uneconomic, time-consuming, of low environmental compatibility and may lead through the rinsing water to recontamination with unwanted microorganisms.

The Patent DRP 649 206 of 5 Aug. 1937 relates to a disinfection method in which a glycerol monoalkyl ether is used as aqueous solution or emulsion, for example for disinfectant treatment of equipment in the food and other consumables industries. The glycerol monoalkyl ethers specifically disclosed are glycerol monododecyl ether, glycerol monodecyl ether, glycerol monooctyl ether, glycerol monobenzyl ether, diglycerol monooctyl ether, glycerol monocyclohexyl ether, and a mixture of glycerol monooctyl, monodecyl and monododecyl ethers. However, at room temperature, glycerol ethers without other agents have virtually no effect on microorganisms or have an effect only with long exposure times—but even then only inhibit microbial growth rather than actually kill microbes.

DRP 649 206 further states that dialkyl ethers of glycerol can be used with equal success. However, the only effect described is for selected glycerol ethers at 50° C. and on the yeast *Mycoderma* and the mould *Oidium lactis* (first table) and on thermobacteria, acetic bacteria, *Penicillium, Oidium, Mycoderma* and cultivated yeast (second table). The test methods are not disclosed. All the bacteria and fungi mentioned in the patent are important in the manufacture of food products where killing with a disinfectant is also occasionally necessary. They are not, however, pathogens and are therefore of no significance in hospitals or medical practices.

Following the teaching of DRP 649 206 and testing the activity of the glycerol ethers disclosed therein using present-day test methods reveals virtually no effect on microbes of hygienic relevance (such as the tubercle bacillus). An additional factor is that the compounds disclosed in DRP 649 206 are, for various practical reasons, useless for a modern (mechanical) thermochemical disinfection method.

For example, monooctyl glycerol ether is associated with the disadvantages that the ether when dissolved in water gives a solution which is always turbid and—which is particularly disadvantageous for modern mechanical thermochemical disinfection methods—highly foaming. DRP 615 171 of 6 Jun. 1935 in fact emphasizes the foam-stabilizing effect in this connection (cf. lines 56 et seq. therein). This has been confirmed for 1-(n-octyl)glycerol ether by the experiments carried out for the purposes of the present invention, which are detailed in the example section.

Dialkyl ethers of glycerol, e.g. dioctyl glycerol ethers, have no solubility in water and are unsuitable for the present object.

Accordingly, no compositions containing glycerol ethers for thermochemical disinfection are known to be on the market, and the monoalkyl glycerol ethers mentioned in DRP 649 206 are not available in commercial quantities. This can also be explained by hindsight and on the basis of the present invention by the facts that glycerol ethers display no micro-bicidal activity at room temperature in acceptable use concentrations, whereas the compositions conventionally used for thermochemical disinfection methods are effective even at room temperature, and the activity was merely improved by raising the temperature. Compositions displaying a very steep temperature gradient (starting from a low or absent activity at room temperature) are not generally known on the market.

DE-A-40 26 756 relates to preservatives which contain as synergistic agents a mixture of a) an organic acid, b) a monophenyl glycol ether and c) a guanidine derivative. Examples 13 and 14 are concentrates with more than 60% by weight of phenoxyethanol and respectively 15 and 10% by weight of glycerol monoalkyl ether. The preservatives in DE-40 26 756 are effective for various bacteria and yeasts. The applicant's post-published DE A-102 24 979 discloses mixtures of glycerol ethers with aromatic alcohols for controlling mycobacteria. Use of the mixtures at elevated temperature is not described.

DE-A-41 40 474 relates to the use of glycerol monoalkyl ethers as refatting skincare additives. DE-A-100 25 122, DE-A-100 25 123 and DE-A-100 25 124 disclose preparations having a content of glycerol monoalkyl ether. The preparations are used for preserving cosmetic and dermatological preparations. DE-C-42 40 674 discloses that glycerol monoalkyl ethers of the formula R—O—CH$_2$—CHOH—CH$_2$OH have a deodorant effect. DE-C-41 40 473 discloses compositions which can be used as skin antiseptics and hand disinfectants and which contain a combination of an aliphatic C$_1$- to C$_6$-alkyl alcohol component and at least one glycerol monoalkyl ether in aqueous solution, and further states that the use of glycerol monoalkyl ethers in preparations containing considerable quantities of water is entirely inadequate without further additions which likewise have antimicrobial activity.

DE-A-41 24 664 describes mixtures having antimicrobial activity and containing a synergistic combination of aryl-substituted alkanol with diol. Exemplary diols are glycerol monoalkyl ethers. The mixtures are used to preserve aqueous preparations of substances susceptible to microbial degradation (oils, fats, proteins, carbohydrates or derivatives thereof).

The present invention was thus based on the object of providing a composition for thermochemical disinfection of surfaces of articles such as instruments and thermolabile materials, which satisfies the stated requirements and avoids the disadvantages of the state of the art. The object was in particular to provide for a (mechanical) thermochemical disinfection method a composition which does not attack or attacks negligibly materials used in the hospital sector as surfaces of articles and which must be disinfected, also above room temperature, and has no irritant or defatting effect on contact with human skin (that is, does not necessarily have a high content of lower alcohols such as ethanol or isopropanol).

SUMMARY OF THE INVENTION

It has now surprisingly been found according to the invention that 1-(2-ethylhexyl)glycerol ether has an exceptionally steep temperature gradient of the micro-bicidal effect. The invention is thus based on the possibility of using a composition which contains 1-(2-ethylhexyl)glycerol ether for disinfecting the surface of an article at a temperature above room temperature (room temperature defined as 25° C.), preferably a temperature of 30° C. or above, more preferably 35° C. or above, in particular 40° C. or above, most preferably 50° C. or above.

DESCRIPTION OF PREFERRED EMBODIMENTS

In one embodiment, the disinfection is carried out without elevated pressure. The disinfection temperature in this case is preferably 40 to 80° C., more preferably 45 to 60° C., in particular 45 to 55° C., for example about 50° C.

In a further embodiment of the invention, the disinfection is carried out under elevated pressure. The disinfection temperature in this case is up to 170° C. and is preferably in the range from 80 to 160° C., more preferably 100 to 150° C., in particular 120 to 140° C., for example 130 to 135° C. At present, a maximum temperature of 134° C. for a period of 20 minutes is regarded as adequate for example for the inactivation of prions, in the case of thermal inactivation.

A sterilization (eradication of viable microbes) of inanimate surfaces above 100° C. can take place for example in an autoclave with superheated, saturated steam or a steam/air mixture under elevated pressure. Thus, for example, a steam sterilization or autoclaving can take place at a minimum of 120° C., corresponding to a gauge pressure of 1 bar, acting for a time of from 15 to 20 minutes with the addition of a composition according to the invention.

The use takes place on inanimate surfaces, e.g. during the thermochemical disinfection and/or cleaning of instruments, thermostable materials and thermolabile materials, such as endoscopes.

The use according to the invention can take place by wetting, spraying, rubbing, wiping or moistening the surface with the composition, dipping the surface into the composition, or disinfecting the surface by atomizing the composition. The treated surface of the article in this connection is any inorganic or organic material, in particular a thermosensitive material, for example made of metal, glass, wood, plastic, textile or ceramic. The article may be a medical instrument or laboratory apparatus, a product system or a part thereof, for example a pipeline or a storage tank, a foodstuffs container such as a bottle, a product which is subject to the Medical Appliances Act, an air-conditioning system, a membrane, an ion exchanger or a cooling water circulation. The use takes place for example in the manual and mechanical disinfection and preparation of medical instruments and appliances, especially thermolabile instruments such as flexible endoscopes.

The use referred to here as disinfection may be any cleaning, preservation, sterilization, instrument preparation, system disinfection or maintenance, but is preferably a mechanical use. The disinfection time is, for example, 10 seconds to 1 hour, more preferably 1 minute to 30 minutes, in particular 5 to 15 minutes.

The thermochemical disinfection of instruments, especially of thermolabile instruments such as flexible endoscopes, is carried out in special automatic cleaning and disinfecting systems. An example of a programme procedure according to the invention, in which the composition is advantageously employed in the form of an instrument disinfectant, is as follows:

1. where appropriate precleaning with cold water,
2. cleaning at 55 to 60° C. with a neutral cleaner (e.g. as 0.5% strength solution),
3. thermochemical disinfection at 55 to 60° C. acting for a time of from 1 to 20 minutes, e.g. about 5 minutes, with a disinfectant (e.g. 1 to 3% strength based on a concentrate),
4. rinsing with cold water and
5. drying.

An alternative method includes the steps of:
1) where appropriate precleaning with cold water,
2) cleaning with a neutral cleaner, raising the temperature to 90 to 100° C., preferably 90 to 95° C., such as about 93° C.,
3) thermochemical disinfection at 90 to 100° C., preferably 90 to 95° C., such as about 93° C., acting for a time of from 1 to 20 minutes with the composition,
4) rinsing with water and
5) drying, where appropriate at 40 to 60° C.

The statements concerning the thermochemical disinfection according to the invention preferably relate to step 3 of the method described above.

The composition employed according to the invention contains, besides (a) 1-(2-ethylhexyl)glycerol ether, where appropriate (b) one or more further agents. Examples of further agents are aldehydes, amines, phenols, halogen compounds and carboxylic acids, and aromatic alcohols, preferably o-phenylphenol, triclosan, o-phthalaldehyde, Lonzabac 12 and Lonzabac LF. A particularly preferred further agent is citric acid (e.g. as monohydrate). The composition (concentrate, solution for use) where appropriate contains no aromatic alcohol.

Besides component (a) and, where appropriate component (b), the composition may contain further components such as (c) one or more auxiliaries. However, it preferably has a low surfactant content and contains less than 5% by weight of surfactant, more preferably less than 2% by weight, particularly less than 0.5% by weight of surfactant, and particularly preferably is free of surfactant (the percentage data are based on the concentrate).

Possible auxiliaries are wetting agents, cleaning components, corrosion inhibitors, surfactants (nonionic surfactants, anionic surfactants, amphoteric surfactants), buffers, acids, alkalizing agents, perfumes, dyes, salts, indicators, markers, complexing agents and antifoams. Exemplary auxiliaries are sodium chloride or sodium hydroxide.

Although concentrates are normally liquid, it is possible to produce pasty or solid concentrates by suitable procedures. In one embodiment of the invention, the composition which is used is in the form of a liquid concentrate and is diluted with water to an aqueous solution for use. Such a concentrate contains, for example, (a) 1 to 20% by weight, such as 2 to 10% by weight, of 1-(2-ethylhexyl)glycerol ether and, where appropriate, up to 40% by weight of water. The skilled person is able to formulate appropriate water-dilutable concentrates with the assistance of suitable auxiliaries such as solvents (glycols such as propylene glycol), solubilizers, acids, alkalizing agents or surfactants. A preferred concentrate is anhydrous.

In another embodiment, the composition is employed as aqueous solution for use and then contains (a) 0.01 to 1.0, more preferably 0.025 to 0.5, in particular 0.05 to 0.2, particularly preferably about 0.1, % by weight of 1-(2-ethylhexyl)glycerol ether and, where appropriate, (b) 0.1 to 15, more preferably 0.5 to 10, in particular 1 to 5, % by weight of one or more further agents. Such a solution for use may contain 80% by weight or more, more preferably 89.5 to 99.45% by weight, in particular 94.9 to 98.9% by weight, of water. Solutions for use preferred in this connection have a pH of from 3 to 10.

A particularly preferred concentrate contains 40 g of citric acid monohydrate, 36 g of deionized water, 20 g of 1,2-propylene glycol and 4 g of 1-(2-ethylhexyl)-glycerol ether. To produce it, the ingredients are stirred until homogeneous at room temperature. A clear colourless liquid is obtained, it being possible to prepare, by dilution of 1 part by weight of concentrate with, for example, 40 parts by weight of water, a clear, 2.5% by weight solution for use which contains 1% by weight of citric acid monohydrate and 0.1% by weight of 1-(2-ethylhexyl)glycerol ether. Accordingly, the use of an aqueous solution for use which comprises (a) 0.05 to 0.2% by weight, such as about 0.1% by weight, of 1-(2-ethylhexyl)glycerol ether and (b) 0.5 to 2.0% by weight, such as about 1% by weight, of citric acid monohydrate is particularly preferred.

In a further embodiment, the composition contains salt. For example, salt-containing compositions may make it possible to control the agent concentration via the electric conductivity. For the inactivation of prions, so-called chaotropic salts are additionally employed. Corrosion-inhibiting salts are able to improve the material compatibility of the compositions.

In the use according to the invention of the composition, the skilled person will choose an optimum between the parameters of use time, concentration of 1-(2-ethylhexyl) glycerol ether and, where appropriate, the components (b) and/or (c), and disinfection temperature, which is consistent with the desired disinfectant action, depending on the sensitivity of the material to be disinfected.

Use of the composition leads to elimination of bacteria (gram-positive and gram-negative), yeasts and moulds, microbacteria and viruses, for example propionibacteria (*Propionibacterium acnes*), dandruff-causing microbes (*Malassezia furfur*), prions, enveloped and/or non-enveloped viruses, odour-causing microorganisms, lower harmful organisms, protozoa and spores.

Results of tests prove that Sensiva SC 50 has a better effect than the glycerol monooctyl ether disclosed in DRP 649 206. Moreover, 1-(2-ethylhexyl)glycerol ether has further advantages:

The substance is economic to use because of the low concentration necessary for use.

The substance is listed in ELINCS and is commercially available worldwide.

The substance has a high purity (<99%) and has been thoroughly investigated and assessed toxicologically.

The substance can be stabilized by adding very small amounts (500 ppm) of vitamin E and is thus stable on storage and contains or forms no degradation products which are toxicologically objectionable, perceptible through odour or material-damaging (formaldehyde, peroxides, 2-ethylhexanol).

The substance is colourless, has a faint odour, is virtually involatile (boiling point <285° C.) and is readily soluble in water (0.18% by weight in water).

In the use according to the invention, the compositions in the form of concentrates have the following advantages:

They can be formulated as liquids and with a high agent content and thus have advantages in terms of handling and cost which would not apply to a concentrate with a high water content.

The concentrates show good colour stability.

The concentrates show a broad spectrum of action even when used in low concentration.

The concentrates are stable at low temperature and are also liquid, pumpable and easily meterable at low temperatures (even at −5° C.).

1-(2-Ethylhexyl)glycerol ether is miscible and compatible in wide ranges with numerous further agents and auxiliaries.

1-(2-Ethylhexyl)glycerol ether acts as wetting agent and assists the disinfectant action also at corners and edges of the surface of the article.

1-(2-Ethylhexyl)glycerol ether is a substance which has been thoroughly investigated toxicologically and has good compatibility with materials in the solution for use.

1-(2-Ethylhexyl)glycerol ether has a high boiling point and high flashpoint, and thus handling the concentrates poses few problems.

The aqueous solutions for use are:
clear, colourless,
low-foaming,
odour- and pH-neutral,
effectively wetting and
oxidation-, pH- and temperature-stable.

The advantages of the present invention are also evident from the following examples:

EXAMPLES

Materials Used:
SC 50=1-(2-Ethylhexyl)glycerol ether, Sensiva SC 50
POE=Phenoxyethanol
Water=Deionized water All percentage data are, unless otherwise indicated, in % by weight.

Test 1

Activity of Disinfectants on Bacteria and Yeasts

Reduction factors were obtained with various solutions for use (SA=*Staphylococcus aureus*, PA=*Pseudomonas aeruginosa*, EC=*Escherichia coli*, CA=*Candida albicans*, AN=*Aspergillus niger*, MT=*Mycobacterium terrae*), initial microbe count 0.8-5×10$^9$/ml, for CA 2×10$^7$/ml, neutralizer Tryp-NaCl-TLSH (No. 22). Concerning the activity on *Mycobacterium terrae*, cf. Test 2.

Method:

0.1 ml of the microbe suspension in CSL is thoroughly mixed at room temperature with 10 ml of the disinfectant dilution to be tested (in water of standardized hardness, WSH). After acting for times of 5, 15, 30 and 60 minutes, 1 ml samples of the disinfectant/microbe mixture are taken and transferred into 9 ml of inactivation liquid (0.1% tryptone+ 0.85% NaCl in double-distilled water+inactivators). After a contact time not exceeding 30 minutes in the inactivation liquid, dilutions (10$^{-2}$ and 10$^{-4}$ in 0.1% tryptone+0.85% NaCl in double-distilled water) are made up. 0.1 ml samples of the inactivation liquid and the two dilutions are then transferred by spatula onto 3 CSA plates for each. As a control, the respective test microbe suspension is mixed with 10 ml of WSH in place of disinfectant. Subcultures are to be set up from this batch in the same way in parallel with the corresponding action times.

All subcultures are incubated at 37° C. for 48 hours, in the case of *Candida albicans* at 37° C. for 72 hours, and the colonies are counted. The reduction is calculated as follows: CFU between 20 and 300 per CSA plate are to be evaluated. After determination of the arithmetic mean of three values, the disinfectant effect (GR$_t$) per unit time is calculated from the formula GR$_t$=log$_{CFU(co)}$ minus log$_{CFU(D)}$ in which CFU (co) is the number of CFU per ml without exposure to the product, and CFU(D) is the number of CFU per ml after exposure to the product.

Test 2

Activity of Disinfectants on *Mycobacterium terrae* at Room Temperature

Various aqueous disinfectants were tested for their activity on *Mycobacterium terrae*, microbe count 1 to 3×10$^9$ in a quantitative suspension test without stress. The *Mycobacterium terrae* (ATCC15755) quantitative suspension test of the Deutsche Gesellschaft füt Hygiene und Mikrobiologie of 30 Apr. 1997 was used (Hyg. Med. 22, 1997, No. 6, pages 278 et seq.). The following reduction factors were measured in this, with a reduction factor of >5 corresponding to adequate activity. The aqueous solutions for use were tested after acting for a defined period. Because of the great structural similarity of *Mycobacterium terrae* with *Mycobacterium tuberculosis*, the results of the activity tests with *Mycobacterium terrae* also provide information on the activity for *Mycobacterium tuberculosis*.

Test 3

Stoppered Cylinder Foam Test

The test is used for qualitative assessment of the foaming behaviour of solutions.

Procedure

The solution to be tested is introduced, avoiding foaming as far as possible, up to the 30 ml mark in a 100 ml measuring cylinder (graduated). It is advisable to hold the cylinder at an angle and allow the solution to run slowly down the wall of the mixing cylinder. The stopper is then inserted.

If foam has nevertheless formed when introducing the solution, the test is not carried out until the foam has completely disappeared. The stoppered cylinder is shaken vigorously 10×, and the stopclock is started. The total volume of solution and foam is then read off in ml after previously specified times.

Example 1 (Comparative)

Activity of Phenoxyethanol on Bacteria, Fungi and Mycobacteria at Room Temperature and 50° C. in a Quantitative Suspension Test The activity of phenoxyethanol (as dilution in water) was investigated. The reduction factors are indicated.

| Microbe | Concentration used (%) | Room temperature | | | 50° C. | | |
|---|---|---|---|---|---|---|---|
| | | 15' | 30' | 60' | 15' | 30' | 60' |
| SA | 0.5 | 0.00 | 0.00 | 0.00 | 0.60 | 0.83 | 0.30 |
| | 0.25 | 0.00 | 0.00 | 0.00 | 0.58 | 0.86 | 0.37 |
| EC | 0.5 | 0.00 | 0.00 | 0.00 | 4.34 | 4.05 | 4.06 |
| | 0.25 | 0.00 | 0.00 | 0.00 | 0.78 | 0.71 | 1.20 |
| PA | 0.5 | 0.00 | 0.00 | 0.00 | 2.67 | 3.74 | 5.18 |
| | 0.25 | 0.00 | 0.00 | 0.00 | 1.11 | 1.27 | 3.49 |
| CA | 0.5 | 0.46 | 0.67 | 0.59 | 0.00 | 1.16 | 1.29 |
| | 0.25 | 0.00 | 0.00 | 0.00 | 0.00 | 0.00 | 1.02 |

-continued

| Microbe | Concentration used (%) | Room temperature | | | 50° C. | | |
|---|---|---|---|---|---|---|---|
| | | 15' | 30' | 60' | 15' | 30' | 60' |
| AN | 0.5 | 0.00 | −0.18 | −0.08 | 0.00 | 0.60 | 0.48 |
| | 0.25 | 0.30 | −0.10 | 0.10 | −0.30 | −0.24 | −0.12 |
| MT | 0.5 | 0.00 | 0.00 | 0.00 | 0.00 | 0.00 | 0.00 |

Result:

Phenoxyethanol in a concentration of 0.5% by weight is active only on gram-negative bacteria even at a temperature of 50° C. and acting for a time of 60 minutes.

Example 2

Activity of SC 50 on Bacteria, Fungi and Mycobacteria at Room Temperature and 50° C. in a Quantitative Suspension Test The activity of SC 50 was investigated. The reduction factors are indicated:

| Microbe | Concentration used (%) | Room temperature | | | 50° C. | | |
|---|---|---|---|---|---|---|---|
| | | 15' | 30' | 60' | 15' | 30' | 60' |
| SA | 0.1 | 0.00 | 0.00 | 0.96 | 2.44 | 4.93 | 4.70 |
| EC | 0.1 | 0.00 | 0.54 | 0.50 | 3.74 | 4.95 | 4.90 |
| PA | 0.1 | 0.00 | 0.00 | 0.00 | 3.55 | 3.50 | 4.00 |
| CA | 0.1 | 0.00 | 0.00 | 0.00 | 1.07 | 1.53 | 4.20 |
| AN | 0.1 | −0.35 | −0.10 | 0.40 | −0.10 | 0.30 | 0.18 |
| MT | 0.1 | 0.00 | 0.00 | 0.00 | 3.10 | 3.34 | 3.48 |

Result:

At low temperature and using the low concentration of 0.1% by weight, SC 50 has virtually no antimicrobial activity. However, even when used in the low concentration, SC 50 has broad activity on gram-positive and gram-negative bacteria, yeasts and mycobacteria even at 50° C.

Example 3 (Comparative)

Lack of Activity of SC 50 for *Mycobacterium terrae* at Room Temperature

Suspension tests were carried out without stress. The reduction factors are indicated below.

| | H$_2$O | | | 10% aqueous EtOH | | | 20% aqueous EtOH | | | 30% aqueous EtOH | | |
|---|---|---|---|---|---|---|---|---|---|---|---|---|
| | 15' | 30' | 60' | 15' | 30' | 60' | 15' | 30' | 60' | 15' | 30' | 60' |
| A | 0 | 0 | 0 | 0 | 0 | 0 | 0 | 0 | 0 | 0.83 | 2.78 | 4.65 |
| B | 0 | 0 | 0 | 0 | 0 | 0 | 0 | 0 | 0.66 | 2.02 | 4.02 | 5.52 |

A no addition
B including 0.1% SC 50

Result:

The data show that SC 50 in a concentration of 0.1% by weight has good activity for *Mycobacterium terrae* at room temperature only on acting for a time of 60 minutes and in a 30% by weight ethanol solution.

Example 4

Activity of a Solution for Use for *Mycobacterium terrae* at 50° C.

Suspension tests were carried out at 50° C. with a concentration of 0.1% by weight SC 50. The reduction factors are indicated below:

| Action for time of 15' | 30' | 60' |
|---|---|---|
| 4.80 | 4.66 | 5.52 |

Result:

The data demonstrate that SC 50 when used in a concentration of only 0.1% by weight is active for *Mycobacterium terrae* at 50° C.

Example 5

Activity of a Solution for Use for *Mycobacterium terrae* at 50° C. in a Quantitative Suspension Test The activity of 1.0% by weight citric acid monohydrate (Comparative Example 5A) and 1.0% by weight citric acid monohydrate mixed with 0.1% by weight SC 50 (Example 5B), each in deionized water, was investigated. The reduction factors are indicated:

| | 1' | 5' | 60' |
|---|---|---|---|
| 5A | 0 | 0 | 0.66 |
| 5B | 0 | 2.07 | 5.11 |

Result:

The data demonstrate that the activity of 1.0% by weight citric acid monohydrate can be reached on use of 0.1% by weight SC 50 at 50° C.

Example 6

Example 6A

Preparation of 1-(n-octyl)glycerol Ether 23 g (1 mol) of sodium were added in portions over the course of 4 hours to 325 g (2.5 mol) of 1-octanol while stirring at 105° C. (the temperature did not rise above 120° C. during this). The mixture was stirred at 115° C. for 1 hour. Subsequently, 110.5 g (1 mol) of 3-chloro-propane-1,2-diol were added over the course of 2 hours, and the mixture was stirred at 120° C. for 3 hours. After cooling, the mixture was taken up in 400 ml of diethyl ether and extracted 3× with a total of 700 ml of water. The ethereal phase was dried over sodium sulphate and concentrated. The residue was distilled in vacuo.

B.p.(15) 137-138° C., 70.5 g, 34.5% of theory, colourless liquid. Faint characteristic odour. Refractive index $n_d^{20}$=1.4517 (Beilstein, Volume 1, IV 2758: 1.4515). The solubility in water is <0.2% by weight and >0.1% by weight.

Example 6B

Direct Comparison of the Foaming Behaviour of SC 50 and 1-(n-octyl)glycerol Ether Test Method
Test 3 at Room Temperature
A) 0.1% by weight 1-(n-octyl)glycerol ether from Example 6A in water
B) 0.1% by weight SC 50 in water.

Result of the Foam Test Carried Out in Duplicate:

|  | Total volume in ml | |
| --- | --- | --- |
| Time/minutes | A | B |
| 0 | 65/70 | 30/30 |
| 1 | 59/62 | 30/30 |
| 2 | 59/60 | 30/30 |
| 3 | 45/44 | 30/30 |
| 5 | 39/38 | 30/30 |
| 10 | 30/30 | 30/30 |

Result: Whereas there is virtually no foam with aqueous SC 50 solution, there is pronounced foaming with an aqueous solution of 1-(n-octyl)glycerol ether.

Example 7

Citric Acid Monohydrate+SC 50, Activity at 60° C.

|  | 7A | 7B | 7C |
| --- | --- | --- | --- |
| SC 50 | 0.1 |  | 0.1 |
| Citric acid × H$_2$O | 1.0 | 1.0 |  |
| Water | 98.9 | 99.0 | 99.9 |

Appearance: all solutions are clear, colourless, faint odour

Quantitative suspension test, microbe *M. terrae*, test temperature 60° C.

Neutralizer: phosphate buffer+TSH-NT, initial microbe count 5☆10$^9$.

|  |  | Values of RF | | | |
| --- | --- | --- | --- | --- | --- |
|  |  | 5' | 15' | 30' | 60' |
| 7A | conc. 50% | 4.33 | 4.23 | 5.28 | 5.25 |
|  |  | 3.60 | 3.30 | 3.12 | 3.64 |
| 7B | conc. 50% | 2.40 | 2.97 | 4.08 | 4.77 |
|  |  | 1.87 | 2.46 | 2.45 | 2.29 |
| 7C | conc. 50% | 5.37 | 5.51 | 5.28 | 5.25 |
|  |  | 3.03 | 2.79 | 4.13 | 5.25 |

Result:
0.1% strength or 0.05% strength aqueous solution of SC 50 has an excellent activity at elevated temperature (e.g. 60° C.). Addition of SC 50 markedly improves the Tb activity of citric acid at 60° C.

The advantages of the SC 50+ citric acid combination are improved activity, wetting, low foam, cleansing action of citric acid, a contribution to the cleansing action of citric acid by SC 50 and improved stability of the aqueous solution (extended endurance).

Example 8

Tb Activity of Sensiva SC 50 in the Alkaline pH Range at 22.5° C. and 50° C.

|  | 8A | 8B |
| --- | --- | --- |
| SC 50 | 0.1 |  |
| 0.5 M NaOH | 20 | 20 |
| Water | 79.9 | 12.8 |
| pH | 12.8 | 12.8 |

Quantitative Suspension Test, Values of Rf for *M. terrae*

|  | 22.5° C. | | | 50° C. | | |
| --- | --- | --- | --- | --- | --- | --- |
|  | 5' | 15' | 60' | 5' | 15' | 60' |
| 8A | 0 | 0.53 | 0.55 | 1.24 | 3.62 | 4.48 |
| 8B | 0 | 0 | 0 | 0.65 | 1.17 | 1.06 |

SC 50 shows excellent activity on *Mycobacterium terrae* above room temperature even in the alkaline range.

It will be understood that many additional changes in the details, materials, steps and arrangement of parts, which have been herein described in order to explain the nature of the invention, may be made by those skilled in the art within the principle and scope of the invention as expressed in the appended claims. Thus, the present invention is not intended to be limited to the specific embodiments in the examples given above.

The invention claimed is:

1. A method for disinfecting the surface of an article comprising:
   contacting said surface for the time of about 5 to 15 minutes with a composition comprising an effective amount of 1-(2-ethyl-hexyl)glycerol ether to disinfect said surface at a temperature from about 100° C. to about 150° C. wherein,
   said composition contacting said surface is not efective to disinfect said surface at 25° C. for said time,
   said surface is inanimate.

2. The method according to claim 1, wherein said composition further comprising at least one component selected from the group consisting of:
   a) additional agent; and
   b) auxiliary.

3. The method according to claim 2, wherein said additional agent is citric acid.

4. The method according to claim 3, wherein said composition contains no aromatic alcohol.

5. The method according to claim 2, wherein said additional agent comprises at least one component selected from the group consisting of:
   a) aldehydes;
   b) amines;
   c) phenols;

d) halogen compounds;
e) carboxylic acids; and
f) aromatic alcohols.

6. The method according to claim 5, wherein said aromatic alcohol comprises at least one component selected from the group consisting of:
   a) o-phenylphenol;
   b) triclosan;
   c) o-phthalaldehyde;
   d) Lonzabac 12; and
   e) Lonzabac LF.

7. The method according to claim 2, wherein said auxiliary comprises at least one component selected from the group consisting of:
   a) aldehydes;
   b) amines;
   c) phenols;
   d) halogen compounds;
   e) carboxylic acids;
   f) wetting agents;
   g) cleaning components;
   h) corrosion inhibitors;
   i) nonionic surfactants;
   j) anionic surfactants;
   k) amphoteric surfactants;
   l) buffers;
   m) acids;
   n) alkalizing agents;
   o) perfumes;
   p) dyes;
   q) salts;
   r) indicators;
   s) markers;
   t) complexing agents; and
   u) antifoams.

8. The method according to claim 7, wherein said auxiliary comprises at least one component selected from the group consisting of:
   a) sodium chloride;
   b) o-phenylphenol;
   c) triclosan;
   d) o-phthaldialdehyde;
   e) Lonzabac 12;
   f) Lonzabac LF;
   g) sodium benzoate; and
   h) sodium hydroxide.

9. The method according to claim 1, wherein said composition is in the form of an aqueous solution.

10. The method according to claim 1, further comprising:
    obtaining an anhydrous form of said composition; and
    diluting said anhydrous form with water to form said composition.

11. The method according to claim 1, wherein said temperature is in the range of from about 45 to about 60° C.

12. The method according to claim 11, wherein said temperature is in the range of from about 45 to about 55° C.

13. The method according to claim 12, wherein said temperature is about 50° C.

14. The method according to claim 1, wherein said surface is wetted, sprayed, rubbed, wiped or moistened with the composition.

15. The method according to claim 1, wherein said surface is dipped into the composition.

16. The method according to claim 1, wherein said surface is disinfected by atomizing the composition.

17. The method according to claim 1, wherein said surface to be disinfected comprises at least one component selected from the group consisting of:
    a) metal;
    b) glass;
    c) wood;
    d) plastic;
    e) textile; and
    f) ceramic.

18. The method according to claim 1, wherein said article to be disinfected is at least one device selected from the group consisting of:
    a) medical instrument;
    b) laboratory apparatus;
    c) thermolabile materials; and
    d) thermostable materials.

19. The method according to claim 1, wherein said article to be disinfected is at least one device selected from the group consisting of:
    a) bottle;
    b) air-conditioning system;
    c) membrane;
    d) ion exchanger;
    e) cooling water circulation; and
    f) endoscope.

20. The method according to claim 1, wherein said time is in the range of from about 10 seconds to about 1 hour.

21. The method according to claim 20, wherein said range is from about 1 minute to about 30 minutes.

22. The method according to claim 21, wherein said range is from about 5 to about 15 minutes.

23. The method according to claim 1, further comprising:
    obtaining a concentrate form of said composition, said concentrate having from about 1 to about 20% by weight of said glycerol ether; and
    diluting said concentrate with water to form said composition.

24. The method according to claim 23, wherein said amount of glycerol ether is from about 2 to about 10% in said concentrate.

25. The method according to claim 1, wherein said composition further comprises about 80% of water by weight.

26. The method according to claim 25, wherein said composition comprises from about 89.5% to about 99.45% water by weight.

27. The method according to claim 26, wherein said composition comprises from about 94.9% to about 98.9% water by weight.

28. The method according to claim 1, further comprising:
    obtaining a concentrate form of said composition, said concentrate comprising up to about 40% of water by weight; and
    diluting said concentrate with water to form said composition.

29. The method according to claim 28, wherein said concentrate is diluted so that said composition comprises from about 94.5 to about 99.725% by weight water.

30. The method according to claim 29, wherein said composition comprises from about 97.8 to about 99.45% by weight water.

31. The method according to claim 2, wherein said composition comprising:
    a) from about 0.01 to about 1.0% of glycerol ether by weight as said effective amount; and
    b) from about 0.1 to about 15% of at least one additional agent by weight.

32. The method according to claim 31, wherein said composition comprises:
a) from about 0.025 to about 0.5% of glycerol ether by weight, and
b) from about 0.5 to about 10% of at least one additional agent by weight.

33. The method according to claim 32, wherein said composition comprises about 0.1% of said glycerol ether by weight as said effective amount of the total composition.

34. The method according to claim 2, wherein said composition further comprises:
c) a salt.

35. The method according to claim 1, wherein said composition has a pH in the range of from about 3 to about 10.

36. The method according to claim 1, wherein said composition disinfects at least one component selected from the group consisting of:
a) bacteria;
b) yeasts;
c) molds;
d) mycobacteria;
e) viruses;
f) propionibacteria (*Propionibacterium acnes*);
g) dandruff-causing microbes (*Malassezia furfur*);
h) prions;
i) odour-causing microorganisms;
j) lower harmful organisms;
k) protozoa;
l) pores; and
m) fungi.

37. A method for disinfecting the surface of an article comprising:
contacting said surface for a time with a composition comprising and effective amount of 1-(2-ethyl-hexyl)glycerol ether to disinfect said surface at an elevated pressure ant a temperature from about 40° C. to about 170° C., wherein,
said composition contacting said surface is not effective to disinfect said surface at 25° C. for said time, and
said surface is inanimate.

38. The method according to claim 37, wherein said temperature is in the range of from about 80 to about 160° C.

39. The method according to claim 38, wherein said temperature is in the range of from about 100 to about 150° C.

40. The method according to claim 39, wherein said temperature is in the range of from about 120 to 140° C.

41. The method according to claim 40, wherein said temperature is in the range of from about 130 to 135° C.

42. A process for the disinfection of an article comprising the steps of:
i) cleaning said article with a neutral cleaner;
ii) disinfecting of said article by thermochemical disinfection with a composition comprising an effective amount of 1-2-ethyl-hexyl) glycerol ether and at least one aromatic alcohol for an operating time, said composition not being capable of disinfecting said article for said operating time abscent thermochemical disinfection;
iii) rinsing said article with cold water; and
iv) drying said article.

43. The process according to claim 42, further comprising the step of precleaning said article with cold water before step i).

44. The process according to claim 42, wherein said cleaning occurs at a temperature in the range of from about 55 to about 60° C.

45. The process according to claim 42, wherein said cleaning occurs at a temperature of about 93° C.

46. The process according to claim 42, wherein said disinfection occurs at an operating temperature in the range of from about 55 to about 60° C.

47. The process according to claim 42, wherein said disinfection occurs at an operating temperature in the range of from about 90 to about 100° C.

48. The process according to claim 47, wherein said temperature is in the range of from about 90 to about 95° C.

49. The process according to claim 42, wherein said drying occurs at an operating temperature of from about 40 to about 60° C.

50. The process according to claim 42, wherein said operating time of from about 1 to about 20 minutes.

* * * * *